(12) United States Patent
Rieker et al.

(10) Patent No.: US 11,813,233 B2
(45) Date of Patent: Nov. 14, 2023

(54) OMEGA 3 FATTY ACIDS AND CHOLINE AS NEUROPROTECTANT IN PATIENTS WITH NO DEMENTIA

(71) Applicant: NESTEC S.A., Vevey (CH)

(72) Inventors: Claus Rieker, St-Sulpice (CH); Julie Hudry-Labbe, Epalinges (CH); Jeroen Antonius Johannes Schmitt, Moudon (CH); Corina Boschat, Lausanne (CH); Yvonne Beata Silber, Essertes (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 16/336,294

(22) PCT Filed: Sep. 29, 2017

(86) PCT No.: PCT/EP2017/074731
§ 371 (c)(1),
(2) Date: Mar. 25, 2019

(87) PCT Pub. No.: WO2018/060396
PCT Pub. Date: Apr. 5, 2018

(65) Prior Publication Data
US 2020/0046660 A1 Feb. 13, 2020

Related U.S. Application Data

(60) Provisional application No. 62/401,443, filed on Sep. 29, 2016, provisional application No. 62/484,119, (Continued)

(51) Int. Cl.
A61K 31/202 (2006.01)
A61K 31/197 (2006.01)
(Continued)

(52) U.S. Cl.
CPC ............ *A61K 31/714* (2013.01); *A61K 31/14* (2013.01); *A61K 31/17* (2013.01); *A61K 31/197* (2013.01);
(Continued)

(58) Field of Classification Search
CPC ... A61K 31/714; A61K 31/197; A61K 31/202
See application file for complete search history.

(56) References Cited

U.S. PATENT DOCUMENTS 8,445,458 B2 5/2013 Hageman et al.
2002/0182196 A1 12/2002 Mccleary
(Continued)

FOREIGN PATENT DOCUMENTS

CN 104703593 A 6/2015
CN 105663151 A 6/2016
(Continued)

OTHER PUBLICATIONS

Web printout of "Adult." Merriam-Webster.com Dictionary, Merriam-Webster, https://www.merriam-webster.com/dictionary/adult. Accessed Mar. 22, 2021, pp. 1-7. (Year: 2021).*

(Continued)

*Primary Examiner* — Craig D Ricci
*Assistant Examiner* — Janet L Coppins
(74) *Attorney, Agent, or Firm* — K&L Gates LLP

(57) ABSTRACT

A method of attenuating, treating or preventing cognitive aging in an individual who does not have dementia includes administering to the individual a therapeutically effective amount of a composition containing an omega-3 fatty acid and choline. The method can achieve a benefit that is one or more of decreasing brain atrophy, increasing or maintaining number of synapses, increasing amyloid-β phagocytosis, or decreasing or maintaining neuroinflammation in the non-demented individual. The method can prevent dementia in (Continued)

an individual at risk thereof, for example an elderly human. The composition can be administered to the individual in a daily dose that provides 5.5 mg/day to 5,500 mg/day of the choline, for example 85 mg/day to 3,500 mg/day of the choline.

11 Claims, 2 Drawing Sheets

Related U.S. Application Data filed on Apr. 11, 2017, provisional application No. 62/484,156, filed on Apr. 11, 2017.

(51) Int. Cl.

| | | |
|---|---|---|
| *A61K 31/519* | (2006.01) | |
| *A61K 31/14* | (2006.01) | |
| *A61K 31/714* | (2006.01) | |
| *A61K 31/198* | (2006.01) | |
| *A61K 31/4415* | (2006.01) | |
| *A61K 31/17* | (2006.01) | |
| *A61K 31/375* | (2006.01) | |
| *A61K 31/4406* | (2006.01) | |
| *A61K 33/00* | (2006.01) | |
| *A61K 31/341* | (2006.01) | |
| *A61K 31/355* | (2006.01) | |
| *A61K 31/4188* | (2006.01) | |
| *A61K 31/455* | (2006.01) | |
| *A61K 31/51* | (2006.01) | |
| *A61K 31/525* | (2006.01) | |
| *A61K 31/59* | (2006.01) | |
| *A61K 31/675* | (2006.01) | |
| *A61K 33/04* | (2006.01) | |

(52) U.S. Cl.
CPC .......... *A61K 31/198* (2013.01); *A61K 31/202* (2013.01); *A61K 31/341* (2013.01); *A61K 31/355* (2013.01); *A61K 31/375* (2013.01); *A61K 31/4188* (2013.01); *A61K 31/4406* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/59* (2013.01); *A61K 31/675* (2013.01); *A61K 33/00* (2013.01); *A61K 33/04* (2013.01)

(56) References Cited

U.S. PATENT DOCUMENTS

| | | | |
|---|---|---|---|
| 2010/0292330 A1 | 11/2010 | Pan et al. | |
| 2011/0257109 A1* | 10/2011 | Wurtman | A61P 25/00 514/25 |
| 2014/0271844 A1 | 9/2014 | Miller | |
| 2015/0086625 A1* | 3/2015 | Miller | A61K 45/06 424/456 |

FOREIGN PATENT DOCUMENTS

| | | | | |
|---|---|---|---|---|
| JP | 2010533647 A | 10/2010 | | |
| JP | 2011508773 A | 3/2011 | | |
| WO | 9926620 | 6/1999 | | |
| WO | 2005037848 A2 | 4/2005 | | |
| WO | 2008005869 | 1/2008 | | |
| WO | 2010143053 | 12/2010 | | |
| WO | WO-2014151364 A1 * | 9/2014 | ........... A61K 31/519 |
| WO | 2016207794 | 12/2016 | | |

OTHER PUBLICATIONS

University of Oxford. "Low omega-3 could explain why some children struggle with reading." ScienceDaily. ScienceDaily, Sep. 13, 2013. <www.sciencedaily.com/releases/2013/09/130913092414.htm> (Year: 2013).*
Phillips et al, Lower omega-3 fatty acid intake and status are associated with poorer cognitive function in older age: A comparison of individuals with and without cognitive impairment and Alzheimer's disease, Nutritional Neuroscience 2012, 15:6, 271-277. (Year: 2012).*
Cao et al., Clinical Chemistry 52:12 2265-2272 (2006) (Year: 2006).*
Oulhaj et al., "Omega-3 Fatty Acid Status Enhances the Prevention of Cognitive Decline by B Vitamins in Mild Cognitive Impairment", Journal of Alzheimer's Disease, vol. 50, Issue No. 2, 2016, pp. 547-557.
Sindi et al., The CAIDE Dementia Risk Score App: The Development of an Evidence-Based Mobile Application to Predict the Risk of Dementia, Alzheimer's & Dementia: Diagnosis, Assessment & Disease Monitoring, vol. 1, Issue No. 3, 2015, pp. 328-333.
Hughes et al., "Vitamin B12 and Ageing: Current Issues and Interaction with Folate", Annals of Clinical Biochemistry, vol. 50, Issue No. 4, 2013, pp. 315-329.
Brazil Patent Office Communication for Application No. BR112019004041-2, dated Aug. 23, 2021, 4 pages.
West et al., "Homocysteine and Cognitive Function in Very Elderly Nondemented Subjects", American Journal of Geriatric Psychiatry, vol. 19, Issue No. 7, Jul. 1, 2011, pp. 673-677, XP055684188.
Bescos et al., "The Effect of Nitric-Oxide-Related Supplements on Human Performance", Sports Medicine, vol. 42, Issue No. 2, Feb. 1, 2012, pp. 99-117, XP055684211.
China Patent Office Communication for Application No. 201780055067.7 dated Dec. 22, 2021, 13 pages.
Wurtman et al., "Synaptic Proteins and Phospholipids are Increased in Gerbil Brain by Administering Uridine Plus Docosahexaenoic Acid Orally", Brain Research, vol. 1088, Issue No. 1, 2006, pp. 83-92.
Japan Patent Office Communication for Application No. P2019-512869, Dispatch No. 651505, Dispatch Date ?Aug. 31, 2021, 8 pages.
Japan Patent Office Communication for Application No. P2019-512869, Dispatch No. 318226, Dispatch Date Jul. 5, 2022, 7 pages.

* cited by examiner treatments

|         | μM   |
|---------|------|
| DHA + EPA | 0.15 |
|         | 1.5  |
|         | 15   |
|         |      |
| Choline | 15   |
|         | 30   |
|         | 300  |
|         |      |

FIG. 1

OMEGA 3 FATTY ACIDS AND CHOLINE AS NEUROPROTECTANT IN PATIENTS WITH NO DEMENTIA

CROSS REFERENCE TO RELATED APPLICATIONS

The present application is a National Stage of International Application No. PCT/EP2017/074731, filed on Sep. 29, 2017, which claims priority to U.S. Provisional Application No. 62/401,443, filed on Sep. 29, 2016, U.S. Provisional Application No. 62/484,119, filed on Apr. 11, 2017, and U.S. Provisional Application No. 62/484,156, filed on Apr. 11, 2017, the entire contents of which are being incorporated herein by reference.

BACKGROUND

The present disclosure generally relates to compositions and methods that attenuate cognitive aging in individuals who do not have dementia. More specifically, the present disclosure relates to attenuating cognitive aging by administering a composition comprising a combination of an omega-3 fatty acid and choline.

Population aging has been a remarkable demographic event. As the growth of the older population has outpaced the total population due to increased longevity, the proportion of older persons relative to the rest of the population has increased considerably due to decreased fertility rates. For example, one in every twelve individuals was at least 60 years of age in 1950, and one in every ten was aged 60 years or older by the end of 2000. By the end of 2050, the number of persons worldwide that is 60 years or over is projected to be one in every five.

Aged or aging individuals frequently suffer some degree of cognitive impairment, including decline in cognitive function that progresses with age; and age-related changes in brain morphology and cerebrovascular function are commonly observed. Cognitive decline has been consistently reported with aging across a range of cognitive domains including processing speed, attention, episodic memory, spatial ability and executive function. Brain imaging studies have revealed that these normal age-related cognitive declines are associated with decreases in both grey and white matter volume in the brain, with the fronto-striatal system most heavily compromised with aging. These decreases in cortical volume can be attributed to a number of detrimental cellular processes involved with normal aging, such as accumulation of damage by free radicals over time leading to oxidative damage, chronic low-grade inflammation, homocysteine accumulation (which when elevated are a risk factor for cognitive impairment and dementia), and decreased mitochondrial efficiency. In addition to direct cellular damage, the brain is also indirectly impaired by insults to micro-vascular structures. It is evident that the pathology of aging and also dementia involves a complexity of these interacting factors, which are linked together. For example, mitochondrial dysfunction leads to increased oxidative stress, and oxidative stress can trigger inflammation and vascular insults.

Furthermore, cognitive decline is an early predictor for Alzheimer pathology and begins before the onset of dementia. In this context, the cognitive composite score represents a reliable means to assess the cognitive decline preceding dementia. Considerable evidence suggests that maintaining brain health and preventing cognitive decline with advancing age may prevent or delay development of dementia due to Alzheimer's disease and other aged related neuropathologies.

Nutrition, education, physical exercise and cognitive exercise have been recently demonstrated as possible intervention to prevent cognitive decline with aging. An abundance of clinical, epidemiological, and individual evidence is in favor of individual nutritional factors that reduce dementia risk and age-related neurodegeneration. However, formal trial testing of nutritional interventions has yielded mixed results (Schmitt et al., Nutrition Reviews 68: S2-S5 (2010).

Several long-term studies have failed to observe any cognitive benefits with interventions using combinations of B6, B12 and folate. McMahon et al. (2006) N Engl J Med, 354(26), 2764-2772, found no effect on cognition in adults aged 65+ after 2 years consumption of a supplement containing folate (1000 µg), Vitamin B12 (500 µg) and B6 (10 mg). Similarly, Hankey et al. (2013) (*Stroke*, 44(8), 2232-2239) found that daily supplementation with folic acid (2000 µg), Vitamin B6 (25 mg), and Vitamin B12 (500 µg), to cognitively unimpaired patients with previous stroke or transient ischemic attack, lowered mean tHcy but had no effect on the incidence of cognitive impairment or cognitive decline, as measured by the MMSE, during a median of 2.8 years.

Several short-term studies have also failed to show an effect of the combination of B6, B12 and folate for improving cognitive function. Lewerin et al. (2005) *Am J Clin Nutr,* 81(5), 1155-1162, found that 4 months of supplementation of folic acid (800 µg), Vitamin B12 (500 µg), and Vitamin B6 (3 mg) had no effect on cognition in older adults (median age 76 years).

SUMMARY

Without being bound by theory, the present inventors believe that prior nutritional interventions attempting to reduce dementia risk and age-related neurodegeneration have focused on the administration of nutrients in isolation rather than together intelligently in combination to catapult the magnitude of effect by nutrient interaction. Moreover, studies investigating the effects of combined ingredients on cognitive function have used a mixture of constituents that all target the same mechanism (e.g. a mix of folate, B12, B6 mix targeting Hcy levels, or a mix of Vitamins C and E targeting oxidative damage), which may be why this evidence is as inconsistent as the single ingredient research. Therefore, the present disclosure is generally directed to a multi-intervention approach whereby each of the nutritional interventions targets a different risk factor associated with cognitive decline.

Accordingly, in a general embodiment, the present disclosure provides a method of attenuating, treating or preventing cognitive aging in a non-demented individual in need thereof or at risk thereof. The method comprises administering to the individual a therapeutically effective amount of a composition comprising an omega-3 fatty acid and choline. The composition can be administered in a daily dose that provides 5.5 mg/day to 5,500 mg/day of the choline.

In an embodiment, the individual is an older adult, for example an elderly human.

In an embodiment, the individual has a low DHA status at baseline. In an embodiment, the individual has a Clinical Dementia Rating (CDR) of 0.5 at baseline. In an embodiment the individual has a plasma homocysteine level at baseline of at least 12 μmol/L. In an embodiment, the individual has a risk score in Cardiovascular Risk Factors, Aging and Dementia (CAIDE) of 10 to 15 at baseline. In an embodiment, the individual is amyloid positive on amyloid PET scans at baseline. In an embodiment, the individual has a genotype indicating risk of cognitive decline.

In an embodiment, the composition is orally administered to the individual daily for at least one month.

In an embodiment, the composition comprises a nitric oxide releasing compound, e.g., citrulline.

In an embodiment, the omega-3 fatty acid comprises a fatty acid selected from the group consisting of docosahexaenoic acid, eicosapentaenoic acid and mixtures thereof.

In an embodiment, the choline is provided by an ingredient selected from the group consisting of choline chloride, choline bitartrate, citicoline (CDP-choline), L-alpha-glycerophosphocholine (Alpha-GPC), lecithin, phosphatidylcholine, and mixtures thereof.

In an embodiment, the composition comprises one or more B vitamins selected from the group consisting of Vitamin B1, Vitamin B2, Vitamin B3, Vitamin B5, Vitamin B6, Vitamin B7, Vitamin B9 and Vitamin B12; optionally all of Vitamin B1, Vitamin B2, Vitamin B3, Vitamin B5, Vitamin B6, Vitamin B7, Vitamin B9 and Vitamin B12.

In an embodiment, the composition comprises one or more antioxidants selected from the group consisting of Vitamin C, Vitamin D, Vitamin E, and selenium.

In another embodiment, the present disclosure provides a method of attenuating, treating or preventing cognitive aging in a non-demented individual in need thereof or at risk thereof, the method comprising administering to the individual a therapeutically effective amount of a composition comprising an omega-3 fatty acid and choline. The omega-3 fatty acid can comprise a fatty acid selected from the group consisting of docosahexaenoic acid, eicosapentaenoic acid and mixtures thereof. The choline can be provided by an ingredient selected from the group consisting of choline chloride, choline bitartrate, citicoline (CDP-choline), L-alpha-glycerophosphocholine (Alpha-GPC), lecithin, phosphatidylcholine, and mixtures thereof. The composition can be administered to the individual in a daily dose that provides 5.5 mg/day to 5,500 mg/day of the choline.

In another embodiment, the present disclosure provides a method of achieving one or more of benefits selected from the group consisting of decreasing brain atrophy, increasing or maintaining number of synapses, increasing or maintaining amyloid-β phagocytosis, and decreasing neuroinflammation in a non-demented individual in need thereof. The present disclosure also provides a method of achieving one or more of the benefits selected from the group consisting of improvement of neuronal fluidity, stimulation of neuronal plasticity and activity, improvement of the anti-inflammatory potential, reduction of reactive oxygen species (ROS), and/or target NO release. The present disclosure also provides a method of achieving one or more of the benefits selected from support or maintenance of cognitive performance, support or maintenance of brain performance, slowing down aging of the brain, support of an active mind and brain fitness, support or maintenance of a healthy brain, enhancement of memory, enhancement of executive functions, enhancement of attention, maintenance of cognitive health, maintenance of brain cellular health, etc. Any of such benefits may be preferably achieved by a method as defined herein, preferably a method of attenuating, treating or preventing cognitive aging in a non-demented individual in need thereof or at risk thereof. The methods comprise administering to the individual a therapeutically effective amount of a composition comprising an omega-3 fatty acid and choline. The omega-3 fatty acid can comprise a fatty acid selected from the group consisting of docosahexaenoic acid, eicosapentaenoic acid and mixtures thereof. The choline can be provided by an ingredient selected from the group consisting of choline chloride, choline bitartrate, citicoline (CDP-choline), L-alpha-glycerophosphocholine (Alpha-GPC), lecithin, phosphatidylcholine, and mixtures thereof. The composition can be administered to the individual in a daily dose that provides 5.5 mg/day to 5,500 mg/day of the choline.

In another embodiment, the present disclosure provides a composition comprising a combination of an omega-3 fatty acid and choline. The composition comprises the combination in an amount effective to attenuate cognitive aging in a non-demented individual. The composition can be a food product comprising an ingredient selected from the group consisting of protein, carbohydrate, fat and combinations thereof. The composition can be a pharmaceutical composition comprising a component selected from the group consisting of pharmaceutically-acceptable carriers, diluents and excipients. The omega-3 fatty acid can comprise a fatty acid selected from the group consisting of docosahexaenoic acid, eicosapentaenoic acid and mixtures thereof. The choline can be provided by an ingredient selected from the group consisting of choline chloride, choline bitartrate, citicoline (CDP-choline), L-alpha-glycerophosphocholine (Alpha-GPC), lecithin, phosphatidylcholine, and mixtures thereof. A daily dose of the composition can provide 5.5 mg/day to 5,500 mg/day of the choline.

In another embodiment, the present disclosure provides a method of making a food composition for attenuating cognitive aging in a non-demented individual. The method comprises adding an effective amount of a combination of an omega-3 fatty acid and choline to at least one ingredient selected from the group consisting of protein, carbohydrate, and fat. The omega-3 fatty acid can comprise a fatty acid selected from the group consisting of docosahexaenoic acid, eicosapentaenoic acid and mixtures thereof. The choline can be provided by an ingredient selected from the group consisting of choline chloride, choline bitartrate, citicoline (CDP-choline), L-alpha-glycerophosphocholine (Alpha-GPC), lecithin, phosphatidylcholine, and mixtures thereof.

In another embodiment, the present disclosure provides a method of making a pharmaceutical composition for attenuating cognitive aging in a non-demented individual, the method comprising adding an effective amount of a combination of an omega-3 fatty acid and choline to at least one component selected from the group consisting of pharmaceutically-acceptable carriers, diluents and excipients. The omega-3 fatty acid can comprise a fatty acid selected from the group consisting of docosahexaenoic acid, eicosapentaenoic acid and mixtures thereof. The choline can be provided by an ingredient selected from the group consisting of choline chloride, choline bitartrate, citicoline (CDP-choline), L-alpha-glycerophosphocholine (Alpha-GPC), lecithin, phosphatidylcholine, and mixtures thereof.

In another embodiment, the present disclosure provides a method of preventing dementia in an individual at risk thereof. The method comprises administering to the individual a therapeutically effective amount of a composition comprising an omega-3 fatty acid and choline. The dementia that is prevented can be selected from the group consisting of Alzheimer's disease, vascular dementia, Lewy body dementia, frontotemporal dementia, and combinations thereof. The omega-3 fatty acid can comprise a fatty acid selected from the group consisting of docosahexaenoic acid, eicosapentaenoic acid and mixtures thereof.

In another embodiment, the present disclosure provides a method of improving cognitive ability in a non-demented individual (e.g., an individual in need thereof), the method comprising administering to the individual a therapeutically effective amount of a composition comprising an omega-3 fatty acid and choline. The omega-3 fatty acid can comprise a fatty acid selected from the group consisting of docosahexaenoic acid, eicosapentaenoic acid and mixtures thereof. The choline can be provided by an ingredient selected from the group consisting of choline chloride, choline bitartrate, citicoline (CDP-choline), L-alpha-glycerophosphocholine (Alpha-GPC), lecithin, phosphatidylcholine, and mixtures thereof.

An advantage of one or more embodiments provided by the present disclosure is to attenuate cognitive aging in non-demented individuals such as an elderly human.

Another advantage of one or more embodiments provided by the present disclosure is to use omega-3 fatty acids such as docosahexaenoic acid (DHA) and eicosapentaenoic acid (EPA) to modulate neuronal membrane fluidity, stimulate neuroplasticity, provide anti-neuroinflammatory effects, and/or reduce brain oxidative stress, in combination with choline to decrease homocysteine levels in the plasma and optionally with a nitric-oxide releasing compound such as arginine or citrulline to protect signal transduction pathways.

Yet another advantage of one or more embodiments provided by the present disclosure is to use a higher amount of and choline relative to known nutritional interventions for cognitive aging.

Still another advantage of one or more embodiments provided by the present disclosure is to decrease brain atrophy and neuroinflammation and increase or maintain amyloid-$\beta$ phagocytosis and the number of synapses in a non-demented individual. In this context, one or more of the benefits achieved hereby are selected from the group consisting of improvement of neuronal fluidity, stimulation of neuronal plasticity and activity, improvement of the anti-inflammatory potential, reduction of reactive oxygen species (ROS), and/or target NO release or from other benefits described herein.

Additional features and advantages are described herein and will be apparent from the following Figures and Detailed Description.

BRIEF DESCRIPTION OF THE FIGURES

FIG. 1 is a table listing the treatments used in the experimental example disclosed herein.

DETAILED DESCRIPTION

Definitions

Figure 2:
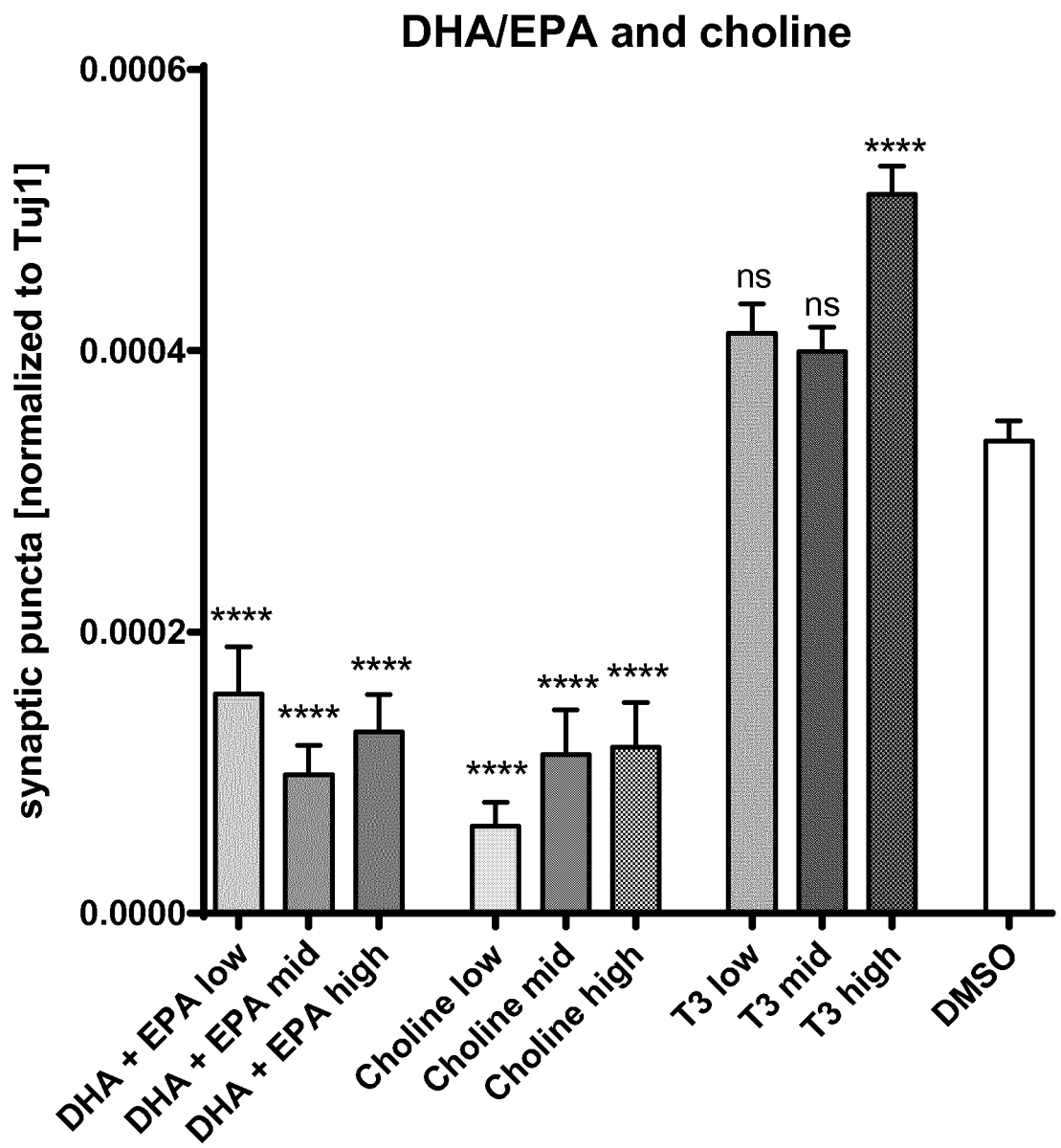
FIG. 2 is a graph showing the results from neurons+ astrocytes in the experimental example disclosed herein (T3=DHA+EPA+choline).

Some definitions are provided hereafter. Nevertheless, definitions may be located in the "Embodiments" section below, and the above header "Definitions" does not mean that such disclosures in the "Embodiments" section are not definitions.

All percentages expressed herein are by weight of the total weight of the composition unless expressed otherwise. As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including" and "or" should all be construed to be inclusive, unless such a construction is clearly prohibited from the context. Nevertheless, the compositions disclosed herein may lack any element that is not specifically disclosed herein. Thus, a disclosure of an embodiment using the term "comprising" includes a disclosure of embodiments "consisting essentially of" and "consisting of" the components identified. A composition "consisting essentially of" contains at least 50 wt. % of the referenced components, preferably at least 75 wt. % of the referenced components, more preferably at least 85 wt. % of the referenced components, most preferably at least 95 wt. % of the referenced components.

The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive.

The terms "food," "food product" and "food composition" mean a product or composition that is intended for ingestion by an individual such as a human and provides at least one nutrient to the individual. The compositions of the present disclosure, including the many embodiments described herein, can comprise, consist of, or consist essentially of the elements disclosed herein, as well as any additional or optional ingredients, components, or elements described herein or otherwise useful in a diet.

"Prevention" includes reduction of risk and/or severity of a condition or disorder. The terms "treatment," "treat," "attenuate" and "alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder, and include treatment of patients at risk of contracting a disease or suspected to have contracted a disease, as well as patients who are ill or have been diagnosed as suffering from a disease or medical condition. The term does not necessarily imply that a subject is treated until total recovery. These terms also refer to the maintenance and/or promotion of health in an individual not suffering from a disease but who may be susceptible to the development of an unhealthy condition. These terms are also intended to include the potentiation or otherwise enhancement of one or more primary prophylactic or therapeutic measure. The terms "treatment," "treat," "attenuate" and "alleviate" are further intended to include the dietary management of a disease or condition or the dietary management for prophylaxis or prevention a disease or condition. A treatment can be patient- or doctor-related.

The term "individual" means any animal, including humans, that could suffer from cognitive aging and thus benefit from one or more of the methods disclosed herein. Generally, the individual is a human or an avian, bovine, canine, equine, feline, hicrine, lupine, murine, ovine or porcine animal. A "companion animal" is any domesticated animal, and includes, without limitation, cats, dogs, rabbits, guinea pigs, ferrets, hamsters, mice, gerbils, horses, cows, goats, sheep, donkeys, pigs, and the like. Preferably, the individual is a human or a companion animal such as a dog or cat.

The term "elderly" in the context of a human means an age from birth of at least 60 years, preferably above 63 years, more preferably above 65 years, and most preferably above 70 years. The term "older adult" in the context of a human means an age from birth of at least 45 years, preferably above 50 years, more preferably above 55 years, and includes elderly individuals.

For other animals, an "older adult" has exceeded 50% of the average lifespan for its particular species and/or breed within a species. An animal is considered "elderly" if it has surpassed 66% of the average expected lifespan, preferably if it has surpassed the 75% of the average expected lifespan, more preferably if it has surpassed 80% of the average expected lifespan. An elderly cat or dog has an age from birth of at least about 7 years.

"Cognitive aging" is a decline in cognitive ability that progresses with age, for example an elderly age that is increasing, and can include age-related changes in brain morphology and/or cerebrovascular function. Cognitive aging does not include impaired cognitive ability caused by an underlying condition other than aging, such as a head injury or depression.

"Cognitive ability" is defined as the intellectual process by which an individual becomes aware of, perceives, or comprehends ideas. Cognitive ability embraces the quality of knowing, which includes all aspects of perception, recognition, conception, sensing, thinking, reasoning, remembering and imaging. Loss of cognitive ability is the difficulty in dealing with or reacting to new information or situations. Cognitive impairment may manifest itself in many ways, e.g., short-term memory loss, diminished capacity to learn, diminished rate of learning, diminished attention, diminished motor performance, and/or dementia, among other indicia. Non-limiting examples of specific cognitive domains that include abilities that decrease with age are (i) attention: processing speed, and selected and divided attention; (ii) learning and memory: delayed free recall, source memory, prospective memory, and episodic memory; (iii) language: verbal fluency, visitation naming, and word finding; (iv) visuospatial abilities: visual construction skills; and (v) executive functioning: planning, decision making, reasoning, and mental flexibility.

As used herein, an "effective amount" is an amount that prevents a deficiency, treats a disease or medical condition in an individual or, more generally, reduces symptoms, manages progression of the diseases or provides a nutritional, physiological, or medical benefit to the individual. The relative terms "improved," "increased," "enhanced" and the like refer to the effects of the composition disclosed herein relative to a composition lacking one or more ingredients and/or having a different amount of one or more ingredients, but otherwise identical.

Embodiments

In an aspect of the present disclosure, a composition comprises a combination of an omega-3 fatty acid and choline; and preferably the composition comprises the combination in an amount effective to attenuate cognitive aging and/or improve cognitive ability in a non-demented individual. In another aspect, a method for attenuating cognitive aging and/or improving cognitive ability in a non-demented individual comprises administering (e.g., orally) an effective amount of the composition to the individual.

In an embodiment, the composition is administered to the individual in a daily dose that provides 0.01 to 10.0 times the recommended daily requirement (RDA) of the choline, for example 0.15 to 6.0 times the RDA of the choline. In this regard, the RDA of choline is 550 mg/day, and thus the composition can be administered in a daily dose that provides 5.5 mg/day to 5,500 mg/day of the choline, for example 85 mg/day to 3,500 mg/day of the choline. Nevertheless, the present disclosure is not limited to a specific daily dose of the choline.

The composition can increase cognitive function in a non-demented individual susceptible to or suffering from a decline in cognitive function brought about by the aging process. The composition can prevent, reduce or delay a decline in cognitive function in a non-demented individual susceptible to or suffering from a decline in cognitive function brought about by the aging process. In some embodiments, the methods comprise, prior to the administration, identifying the individual as having cognitive aging or being at risk of the cognitive aging. For example, the methods can comprise, prior to the administration, identifying the individual as being in need of improved cognitive ability. The composition can decrease brain atrophy and neuroinflammation and increase amyloid-$\beta$ phagocytosis and the number of synapses.

For example, the present disclosure provides a method of treating cognitive aging in a non-demented individual in need thereof (e.g., having cognitive aging), the method comprising administering to the individual a therapeutically effective amount of a composition comprising an omega-3 fatty acid and choline. As another example, the present disclosure provides a method of preventing cognitive aging in a non-demented individual at risk thereof (e.g., an older adult or an elderly individual but not yet having cognitive aging), the method comprising administering to the individual a therapeutically effective amount of a composition comprising an omega-3 fatty acid and choline. As yet another example, the present disclosure provides a method of improving cognitive ability in a non-demented individual (e.g., an individual in need thereof), the method comprising administering to the individual a therapeutically effective amount of a composition comprising an omega-3 fatty acid and choline.

A "non-demented" individual has a Clinical Dementia Rating of up to 0.5. The CDR measures dementia severity and is a global rating of dementia with scores ranging from 0 to 3 (0, 0.5, 1, 2, and 3) rated by a semi-structured subject and informant interview. Hughes et al., Br. J. Psychiatry 140:566-72 (1982). A clinician synthesizes the cognitive and functional abilities based on six domains, including memory, orientation, judgment and problem solving, community affairs, home and hobbies, and personal care. The scale has good inter-rater agreement.

The non-demented individual does not have any of Alzheimer's disease, vascular dementia, Lewy body dementia, or frontotemporal dementia. In some embodiments, the non-demented individual is a healthy aging individual. In other embodiments, the non-demented individual has a phenotype associated with age-related cognitive impairment. For example, when compared to a control individual not having the phenotype, the non-demented individual may have a phenotype that includes one or more of decreased ability to recall, short-term memory loss, decreased learning rate, decreased capacity for learning, decreased problem solving skills, decreased attention span, decreased motor performance, or increased confusion.

A non-limiting example of a non-demented individual at risk of cognitive aging is a human with spontaneous memory complaints but who nevertheless has a Mini Mental State Examination (MMSE) score of at least 24 and has independence in basic daily activities as shown by an Activities of Daily Living (ADL) score of at least 4. An MMSE score for the present purpose may be e.g. 24 to 30, more preferably 26 to 30.

The MMSE is a very brief, easily administered/executed mental status examination that has proved to be a highly reliable and valid instrument for detecting and tracking the progression of the cognitive impairment associated with neurodegenerative diseases. The MMSE is a fully structured scale that consists of 30 points grouped into seven categories: orientation to place (state, county, town, hospital, and floor), orientation to time (year, season, month, day, and date), registration (immediately repeating three words), attention and concentration (serially subtracting 7, beginning with 100, or, alternatively, spelling the word world backward), recall (recalling the previously repeated three words), language (naming two items, repeating a phrase, reading aloud and understanding a sentence, writing a sentence, and following a three-step command), and visual construction (copying a design). Folstein et al., J. Psychiat. Res. 12:189-198 (1975).

The MMSE is scored in terms of the number of correctly completed items; lower scores indicate poorer performance and greater cognitive impairment. The total score ranges from 0 to 30.

The ADL is an informant-based activity of daily living scale widely used measure to assess activities of daily living in people with and without AD. The instrument assesses ability over a wide range of performances. The ADL has shown sensitivity to change among mildly impaired individuals compared to non-impaired controls and can capture functional changes. Galasko et al., Alzheimer Dis. Assoc. Disord. 11 Suppl. 2:S33-9 (1997).

As noted earlier herein, considerable evidence suggests that maintaining brain health and preventing cognitive decline with advancing age may prevent or delay development of dementia. Therefore, the methods disclosed herein which treat or prevent cognitive aging can also ultimately prevent dementia such as Alzheimer's disease. Accordingly, another aspect of the present disclosure is a method of preventing dementia in an individual at risk thereof. The method comprises administering to the individual a therapeutically effective amount of the composition disclosed herein. The dementia that is prevented can be selected from the group consisting of Alzheimer's disease, vascular dementia, Lewy body dementia, frontotemporal dementia, and combinations thereof. The methods preferably comprise administering compositions as described herein.

In an embodiment, the individual has the individual has a low DHA status (erythrocyte omega 3 index<4.8%) at baseline. In an embodiment, the individual has a Clinical Dementia Rating (CDR) of 0.5 at baseline. In an embodiment, the individual has a high plasma homocysteine level at baseline. As used herein, a "high" plasma homocysteine level is plasma homocysteine of at least 12 μmol/L. In another embodiment, the individual has a CAIDE (Cardiovascular Risk Factors, Aging and Dementia) risk score of 10-15 at baseline. In yet another embodiment, the individual is amyloid positive on amyloid PET scans at baseline. In yet another embodiment, the individual has a genotype indicating risk of cognitive decline (e.g., Apolipoprotein E (APOE) genotype).

In various embodiments, the omega-3 fatty acid is 1 to 50 wt. % of the composition, preferably 1 to 30 wt. % of the composition, and most preferably 1 to 15 wt. % of the composition. Preferably, the omega-3 fatty acid comprises at least one of eicosapentaenoic acid (EPA) or docosahexaenoic acid (DHA) and more preferably comprises both EPA and DHA, each of which has anti-inflammatory properties. A daily dose of the composition preferably provides 0.5 g to 1.0 g of DHA per day and/or 0.5 g to 1.0 g of EPA per day, more preferably 0.7 g to 1.0 g of DHA per day and/or 0.6 mg to 0.75 g of EPA per day, and most preferably about 770 mg of DHA per day and/or about 700 mg of EPA per day.

The omega-3 fatty acid may comprise a blend of one or more sources of omega-3 fatty acids, and each of the one or more sources of omega-3 fatty acids can be natural (e.g., fish oil) or synthetic (i.e., formed through a chemical process manipulated by a human, as opposed to those of natural origin). The term "fish oil" means a crude or purified fatty or oily extract rich in omega-3 fatty acids and obtained from a sea individual, preferably a cold-water fish such as, but not limited to, salmon, tuna, mackerel, herring, sea bass, striped bass, halibut, catfish, and sardines, as well as shark, shrimp, and clams, or any combination thereof.

Non-limiting examples of suitable sources of choline that can be used in the composition include choline chloride, choline bitartrate, citicoline (CDP-choline), L-alpha-glycerophosphocholine (Alpha-GPC), lecithin, phosphatidylcholine, and mixtures thereof.

In an embodiment, the composition can optionally comprise a nitric oxide releasing compound. The nitric oxide releasing compound is any compound or compounds that cause or can result in the release of nitric oxide in an individual. The nitric oxide releasing compound preferably comprises one or more of arginine, citrulline, ornithine, or a peptide or protein containing at least one of these amino acids, more preferably arginine and/or citrulline, and even more preferably comprises citrulline, which provides beneficial effects on the cardiovascular system, specifically in terms of improving blood flow, endothelial function and blood pressure. In various embodiments, the nitric oxide releasing compound is 1 to 20 wt. % of the composition, preferably 1 to 15 wt. % of the composition, and more preferably 1 to 10 wt. % of the composition. In an embodiment, a daily dose of the composition provides from 0.5 g to 10.0 g of the nitric oxide releasing compound (e.g., citrulline) per day, preferably 1.0 g to 5.0 g per day, more preferably 2.0 g to 4.0 g per day, and most preferably about 3.0 g per day.

The composition can further comprise at least one B Vitamin, for example one or more of Vitamin B1 (thiamine), Vitamin B2 (riboflavin), Vitamin B3 (niacin), Vitamin B5 (pantothenic acid), Vitamin B6 (pyridoxine), Vitamin B7 (biotin), Vitamin B9 (folate) and Vitamin B12 (Cobalamin) or salts, conjugates or derivatives thereof that have B vitamin activity. The composition can comprise from 0.1 to 40 times the RDA of one or more of these additional B vitamins, preferably 1 to 20 times the RDA, and more preferably 1 to 10 times the RDA. In an embodiment, the composition further comprises all of Vitamin B1 (thiamine), Vitamin B2 (riboflavin), Vitamin B3 (niacin), Vitamin B5 (pantothenic acid), Vitamin B6 (pyridoxine), Vitamin B7 (biotin), Vitamin B9 (folate) and Vitamin B12 (cobalamin).

In this context, the composition may e.g. further contain at least one B Vitamin selected from Vitamin B6, Vitamin B9 and/or Vitamin B12, wherein the composition is preferably administered to the individual in a daily dose that provides at least 0.01 to 100 times the recommended daily requirement (RDA) of the Vitamin B6 per day, for example 10 to 80 times the RDA of the Vitamin B6, and/or 0.01 to 5.0 times the RDA of the Vitamin B9 per day, for example 1.0 to 2.5 times the RDA of the Vitamin B9, and/or 0.1 to 40 times the recommended daily requirement (RDA) of Vitamin B12 per day.

Typically, the amount of Vitamin B12 per day in the inventive composition is 0.1 to 40, preferably 10 to 40, more preferably 10 to 30 or even more preferably 10 to 25 times the RDA of the Vitamin B12 per day, most preferably about 12 to 21 times the RDA of the Vitamin B12 per day. In this regard, the United States RDA of Vitamin B12 is 2.4 micrograms daily for humans of age 14 years and older, such that individuals may be administered a daily dose of the composition that provides also about 0.002 mg to about 0.4 mg of Vitamin B12 per day, preferably 0.02 mg to 0.07 mg of Vitamin B12 per day, more preferably 0.03 mg to 0.05 mg of Vitamin B12 per day. Moreover, the RDA of Vitamin B6 is 1.3 mg/day, the RDA of Vitamin B9 is 0.4 mg/day.

The composition can also comprise from 40 to 500 times, e.g. 40 to 50 times or even 50 to 500 times the RDA of Vitamin B12. The daily dose may then provide about 200 times the RDA of the Vitamin B12 per day, e.g. between 100 and 300 times or preferably between 150 and 250 times the recommended daily requirement (RDA) of Vitamin B12 per day. In this context, individuals may be administered a daily dose of the composition that provides 0.1 mg to 1.5 mg of Vitamin B12 per day, preferably 0.2 mg to 1.2 mg of Vitamin B12 per day, more preferably 0.4 mg to 1.0 mg of Vitamin B12 per day, and most preferably about 0.5 mg of Vitamin B12 per day.

In some embodiments, the composition can further comprise one or more antioxidants to protect against oxidative damage and inflammation-induced damage. Non-limiting examples of suitable antioxidants include Vitamin C, Vitamin D, Vitamin E, selenium, and combinations thereof. The composition can comprise 0.0001 wt. % to 25 wt. % of the antioxidant, if present; preferably 0.0001 wt. % to about 15 wt. %; more preferably 0.001 wt. % to 5 wt. %; and most preferably 0.001 wt. % to 2 wt. %.

In some embodiments, the composition is a food composition for a human and/or a pet such as a companion individual. The food composition may comprise one or more additional substances such as a mineral, another vitamin, a salt, or a functional additive such as flavoring, a colorant, an emulsifier, or an antimicrobial compound or other preservative. Non-limiting examples of suitable minerals include calcium, phosphorous, potassium, sodium, iron, chloride, boron, copper, zinc, magnesium, manganese and iodine. Non-limiting examples of suitable additional vitamins include fat soluble vitamins as A, D, E and K.

In another embodiment, the composition is a pharmaceutical composition comprising one or more pharmaceutically-acceptable carriers, diluents, or excipients. Generally, pharmaceutical compositions are prepared by admixing the omega-3 fatty acid and the choline with one or more of an excipient, a buffer, a binder, a plasticizer, a colorant, a diluent, a compressing agent, a lubricant, a flavorant, or a moistening agent.

The composition can have an acute effect that can be seen in less than one month. Additionally or alternatively, the composition can have a long-term effect, and thus various embodiments comprise administration of the composition to the individual (e.g., orally) for a time period of at least one month; preferably at least two months, more preferably at least three, four, five or six months; most preferably for at least one year. During the time period, the composition can be administered to the individual at least one day per week; preferably at least two days per week, more preferably at least three, four, five or six days per week; most preferably seven days per week. The composition can be administered in a single dose per day or in multiple separate doses per day.

Any of the embodiments as defined herein, particularly ingredients of the described compositions may be combined with each other, if not otherwise described. This also applies with regard to the features and benefits of the methods and treatments defined herein employing such compositions.

EXAMPLE

Example 1

The following non-limiting example is an experimental example supporting attenuation of cognitive aging in a non-demented individual by embodiments of the composition comprising an omega-3 fatty acid and choline that is provided by the present disclosure.

Specifically, the experimental study compared the effects of selected ingredients alone and in combination on synapse formation in human iPSC-derived neuronal culture+astrocytes. Cells were grown for two weeks (neurons+astrocytes) and then the media was replaced with custom-made media. Treatment was performed for 48 hours (n=8), followed by immunocytochemistry+high content imaging+image analysis. FIG. 1 provides a table showing the treatments. As shown in FIG. 2, combining DHA+EPA and choline (T3) strongly increased synapse number at high concentration.

Example 2

The following non-limiting example is illustrative of compositions for attenuating cognitive aging in a non-demented individual, in embodiments provided by the present disclosure.

| Ingredient | Dose/Day |
|---|---|
| DHA | 770 mg |
| EPA | 700 mg |
| Vitamin B1 (thiamin) | 50 mg |
| Vitamin B2 (riboflavin) | 15 mg |
| Vitamin B3 (niacin) | 25 mg |
| Vitamin B5 (pantothenic acid) | 23 mg |
| Vitamin B6 (pyridoxine) | 18 mg |
| Vitamin B7 (biotin) | 0.15 mg |
| Vitamin B9 (folic acid anhydrous) | 0.4 mg |
| Vitamin B12 (cobalamin) | about 12 to 21 times RDA of VitB12 |
| Vitamin C | 500 mg |
| Vitamin D | 0.015 mg |
| Vitamin E | 82.6 mg |
| Selenium | 0.08 mg |
| Citrulline | 3000 mg |
| Choline bitartrate | 85 mg |

Example 3

A study will be conducted in which the primary objective is to demonstrate the efficacy of a 4-year intervention with the composition set forth in Example 2 to prevent cognitive decline as measured by a composite score of neuropsychological assessments. The total study population will consist of non-demented adults with subjective memory concerns aged 70+ years, with a subgroup of the study population defined by low DHA status (erythrocyte omega 3 index<4.8%) at baseline, and another subgroup of the study population with a Clinical Dementia Rating (CDR) of 0.5 at baseline.

Trial design will be a placebo-controlled, double-blind, randomized, multicenter, 2 parallel groups study. The subjects will be randomly allocated to one of two treatment groups (placebo and BPB).

Subjects will be randomized to one of the investigational products: the composition representative of Example 2 or a placebo product. The active and placebo investigational products are composed of one sachet containing a powdered drink mix to be reconstituted in cold water and two soft gel capsules.

In the composition representative of Example 2, the soft gel capsules provide DHA and EPA. The powdered drink contains the rest of the active ingredients with auxiliary ingredients (sucrose, flavors and sweeteners).

In the placebo product, the soft gel capsules contain a mix of vegetable oil free of DHA and EPA but with a similar profile in fatty acid as in the active capsules. The powdered drink does not contain any of the active ingredients and is matched for carbohydrate content to the active powdered drink. It is composed of sucrose/starch, polydextrose, proteins, flavors, natural colorant and sweeteners to be as close as possible to the taste, texture and appearance of the active powdered drink.

The investigational product is taken once daily: one powdered drink and two capsules at the same moment of the day.

During the study, participants will not be permitted to take additional dietary supplements containing B-vitamins: Thiamin (B1), Riboflavin (B2), Niacin (B3), Pantothenic acid (B5), Pyridoxine (B6), Biotin (B7), Folic acid (B9), Cobalamin (B12), DHA, EPA.

The primary endpoint will be the change in a composite score of cognitive assessments at 4-years. The composite score combines the scores in the following neuropsychological tests: learning tests, orientation score, Digit Symbol Substitution test, Category Naming Test. The primary outcome will be looked at the 3 groups (total study population; low DHA status, CDR of 0.5 at baseline).

Secondary endpoints supporting the primary objective will also be studied, specifically
 (i) treatment effects on plasma nutrient levels and biomarkers (e.g. homocysteine, Red blood cell (RBC) DHA status) related to BPB intervention;
 (ii) treatment effects as measured by separate analyses of test outcomes used in the composite score as well as additional neuropsychological test scores: MMSE total score;
 (iii) Trail Making Test, Logical Memory Test, Letter Fluency, Stroop Test, and Digit Span;
 (iv) treatment effects as measured by changes in CDR-SOB (Clinical Dementia Rating-Sum of Boxes) scores; and conversion rates to mild cognitive impairment (MCI) and dementia;
 (v) treatment effects on participant reported outcomes on function and Quality of Life: Cognitive Function Instrument; EQ-5D-5L; and Applied Cognition-Abilities instruments;
 (vi) treatment effects in subgroups defined by the following subject characteristics: high plasma homocysteine levels (plasma homocysteine≥12 μmol/L) at baseline, CAIDE (Cardiovascular Risk Factors, Aging and Dementia) risk score at baseline, amyloid positive on amyloid PET scans at baseline, and genotype.

Further in this regard, biomarkers will be measured, specifically (i) MRI-derived total brain and hippocampal atrophy, and total white matter hyperintensities accumulation, Arterial Spin Labeling imaging, Resting State fMRI in a representative subset of the study population (up to 500 subjects per arm); (ii) Amyloid/Tau PET in a representative subset of the study population (up to 500 subjects per arm); and (iii) blood plasma markers, namely plasma BDNF, plasma Aβ40-42 and Tau protein, asymmetric dimethylarginine, homocysteine, plasma inflammatory markers (sCAMs, E-Selectin, TNFalpha, IL1, IL6, IL10, CRP), and plasma markers of oxidative stress (oxidized low-density lipoprotein (oxLDL), F2-isoprostane).

Secondary exploratory endpoints will include physical function (SPPB), frailty (Fried), anxiety and depression (Geriatric Depression Scale (GDS), Neuropsychiatric inventory questionnaire (NPI-Q)), collect and bank blood and Deoxyribonucleic Acid (DNA) for future research; and effect modification by genetic (single nucleotide polymorphisms e.g., ApoE-84, MTHFR, CBS, FAD1/2, other specific genes identified through novel scientific discoveries) or medical (disease states, e.g. diabetes, cardiovascular disease, hypertension).

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of achieving a benefit selected from the group consisting of decreasing brain atrophy, increasing or maintaining number of synapses, and combinations thereof, in a non-demented individual in need thereof, the method comprising administering to the non-demented individual a therapeutically effective amount of a composition comprising an omega-3 fatty acid, choline, and a B vitamin, the composition is administered to the individual in a daily dose that provides 85 mg of choline per day, 770 mg of docosahexaenoic acid (DHA) per day, 770 mg of eicosapentaenoic acid (EPA) per day, and 0.03 mg to 0.05 mg of Vitamin B12 per day, the non-demented individual is an older adult and has an erythrocyte omega 3 index<4.8% at baseline.

2. The method of claim 1, wherein the B vitamin further comprises an additional B vitamin selected from the group consisting of Vitamin B1, Vitamin B2, Vitamin B3, Vitamin B5, Vitamin B6, Vitamin B7, Vitamin B9, and mixtures thereof.

3. The method of claim 1, wherein the method achieves the benefit of increasing or maintaining number of synapses.

4. The method of claim 1, wherein the choline comprises a choline bitartrate.

5. The method of claim 1, wherein the composition does not contain a nitric oxide releasing compound.

6. The method of claim 1, wherein the composition comprises an antioxidant selected from the group consisting of Vitamin C, Vitamin D, Vitamin E, selenium, and mixtures thereof.

7. The method of claim 1, wherein the non-demented individual has a Clinical Dementia Rating (CDR) of 0.5 at baseline.

8. The method of claim 1, wherein the non-demented individual has a plasma homocysteine level at baseline of at least 12 µmol/L.

9. The method of claim 1, wherein the non-demented individual has a risk score in Cardiovascular Risk Factors, Aging and Dementia (CAIDE) of 10 to 15 at baseline.

10. The method of claim 1, wherein the non-demented individual is an elderly human.

11. The method of claim 1, wherein the choline is provided by an ingredient of the composition selected from the group consisting of choline chloride, choline bitartrate, citicoline, L-alpha-glycerophosphocholine, lecithin, phosphatidylcholine, and mixtures thereof.

* * * * *